United States Patent [19]
Stahl

[11] Patent Number: 5,090,425
[45] Date of Patent: Feb. 25, 1992

[54] METHOD OF CONTROLLING ASTIGMATISM DURING EYE SURGERY

[76] Inventor: Norman O. Stahl, 3199 Monterey Dr., Merrick, N.Y. 11566

[21] Appl. No.: 487,621

[22] Filed: Mar. 2, 1990

[51] Int. Cl.⁵ ............................................. A61B 17/32
[52] U.S. Cl. .................................... 128/898; 606/148; 606/166
[58] Field of Search ...................... 606/166, 148, 4, 5; 128/898

[56] References Cited

U.S. PATENT DOCUMENTS

| | | |
|---|---|---|
| 4,127,109 | 11/1978 | Fourney et al. |
| 4,515,157 | 5/1985 | Fedorov et al. |
| 4,671,276 | 6/1987 | Reynolds |
| 4,705,035 | 11/1987 | Givens |
| 4,766,895 | 8/1988 | Reynolds |
| 4,880,017 | 11/1989 | Soll et al. ............ 128/898 |

FOREIGN PATENT DOCUMENTS

| | | | |
|---|---|---|---|
| 449719 | 11/1974 | U.S.S.R. | 128/898 |
| 450574 | 11/1974 | U.S.S.R. | 128/898 |
| 519194 | 6/1976 | U.S.S.R. | 128/898 |
| 1126298 | 11/1984 | U.S.S.R. | 128/898 |
| 1192819 | 11/1985 | U.S.S.R. | 128/898 |
| 1419697 | 8/1988 | U.S.S.R. | 128/898 |
| 1468531 | 3/1989 | U.S.S.R. | 128/898 |
| 1475660 | 4/1989 | U.S.S.R. | 128/898 |

OTHER PUBLICATIONS

"Corneal Surgery", Louis J. Girard, 1981, pp. 149-153.
Visitec 1990 Catalog cover p. 21.
Journal of Ophthalmic Nursing & Technology 1990; vol. 9, No. 4, p. 179.

*Primary Examiner*—Michael H. Thaler
*Attorney, Agent, or Firm*—Hoffmann & Baron

[57] ABSTRACT

A method of controlling astigmatism during eye surgery is provided which includes forming a wave-like incision prior to conducting surgery. Once the surgery has been completed, the wave-like incision may be stitched in a direction which is substantially parallel to the lengthwise direction of incision to avoid generating a force upon the cornea, which would tend to induce astigmatism. Astigmatism can be induced by stitching in a direction which tends to displace the tissue on opposite sides of the incision by a selected distance. Indicator lines may be applied with a sterile dye prior to surgery to allow the surgeon to insure that the tissue is not displaced when the incision is closed, or is displaced by a selected distance as may be determined by viewing the indicator lines. A marking tool is provided for marking both a wave-like outline which is used for making the incision and the indicator lines for determining relative tissue displacement.

11 Claims, 4 Drawing Sheets

METHOD OF CONTROLLING ASTIGMATISM DURING EYE SURGERY

BACKGROUND OF THE INVENTION

1. Field of the Invention

The field of the invention relates to a method of controlling astigmatism during eye surgery.

2. Brief description of the prior art.

Astigmatism is a condition of the eye caused by the nonspherical shape of the cornea. This causes it to refract light in different meridians at different distances. While all people have some degree of astigmatism, correction of the condition is sometimes required by eyeglasses, contact lenses or surgery. Most astigmatism is below three diopters. Surgical techniques for correcting astigmatism include, among others, refractive keratoplasty and radial keratometry.

Certain types of eye surgery unrelated to the correction of astigmatism require that incisions be made in the tissue adjacent the cornea or in the corneal tissue itself. Such incisions are often between twelve and fourteen millimeters in length, and generally follow the periphery of the cornea. Other types of surgery, such as phacoemulsification, require a three to four millimeter incision. Upon completion of the surgery, the incision is closed by a plurality of stitches which are typically spaced about two millimeters apart. Each stitch is oriented either substantially normal to the peripheral edge of the cornea or at an angle with respect thereto.

If a corneal wound closure is too loose following surgery, it will tend to leak fluids and thereby delay the patient's recovery. In site complications and post-operative astigmatism may also result. Tight closure will cause postoperative astigmatism due to the direction(s) of orientation of the stitches and the force the stitches impart upon the cornea.

A system of controlling astigmatism following cataract surgery is described in U.S. Pat. No. 4,127,109. The incision in the scleral area is often generally arcuate, which is typical of most relatively large incisions in this type of operation. The incision is closed by a length of suture material which provides an opposing continuous pattern. This pattern is said to produce a standard or no deviation of astigmatism from the pre-operative level. The patented system requires the use of a length of suture material which includes a plurality of sets of closely spaced, parallel lines. By observing the suture through a microscope having a reticule disposed therein, the strain in the length of suture material can be determined. Strain and tension data must then be correlated to astigmatism changes.

Other methods of controlling corneal curvature are described in U.S. Pat. Nos. 4,671,276, 4,739,761 and 4,766,895. The '761 patent discloses the use of a cornea marker as part of a procedure for conducting radial and chordal refractive keratomy.

SUMMARY OF THE INVENTION

It is an object of the invention to provide a method of controlling astigmatism during and after eye surgery.

It is another object of the invention to provide a suturing technique which allows a surgeon to either avoid changing a patient's astigmatism from a pre-operative level or to adjust the curvature of the cornea in a controlled manner to correct for pre-existing astigmatism.

A still further object of the invention is to provide a technique which includes making an incision which tends to lock the tissue in place upon closure thereof.

In accordance with these and other objects of the invention, a method is provided which includes the steps of forming an incision within eye tissue such that the incision includes at least one pair of opposing incision portions and a flap of tissue between the opposing incision portions, and suturing the flap to the surrounding eye tissue.

In accordance with a preferred embodiment of the invention, an incision pattern is provided upon the sclera prior to forming the incision. The pattern is preferably applied in the form of a sterile dye. A diamond knife or the like is used to follow the marked pattern. The marked pattern preferably includes markings in the form of indicator lines formed adjacent to the opposing incision portions defining each flap. The indicator lines are employed when the incision is sutured. If no change in astigmatism is desired, the indicator lines will be in the same relative positions following suturing as they were when originally marked. If the surgeon wishes to change the curvature of the cornea, the suturing procedure can be accomplished in such a manner that different indicator lines on opposite sides of the incision will be aligned with each other. The curvature adjustment, if any, is controlled by insuring that the appropriate indicator lines are in proper alignment when the incision is closed.

A marking instrument is also provided by the invention for marking the eye with an incision pattern. The instrument includes a foot portion connected to a handle. The foot portion includes a marking surface which, after being coated with a dye and moved into contact with the sclera, leaves an incision pattern including a plurality of opposing incision lines. The foot portion also preferably leaves a plurality of indicator lines extending, respectively, across the opposing incision lines.

DETAILED DESCRIPTION OF THE INVENTION

The invention relates to a method of controlling astigmatism during eye surgery. Various types of eye surgery require an incision adjacent the cornea of the eye. These include cataract surgery and glaucoma surgery. The size of the incision varies depending upon the type of surgery and the particular operative technique utilized. For example, cataract surgery performed through the use of phacoemulsification requires a relatively small incision of about three millimeters. Other types of eye surgery often require an incision of twelve to fourteen millimeters.

Upon completion of an operation, the incision is sutured closed. Suturing performed in the traditional manner causes the surrounding tissue to be pulled towards the incision. When an incision near the cornea is tightly closed, the curvature of the cornea is affected, thereby causing astigmatism. This problem is more pronounced when closing relatively large wounds, or when the sutures are loosely tightened.

Figure 1:
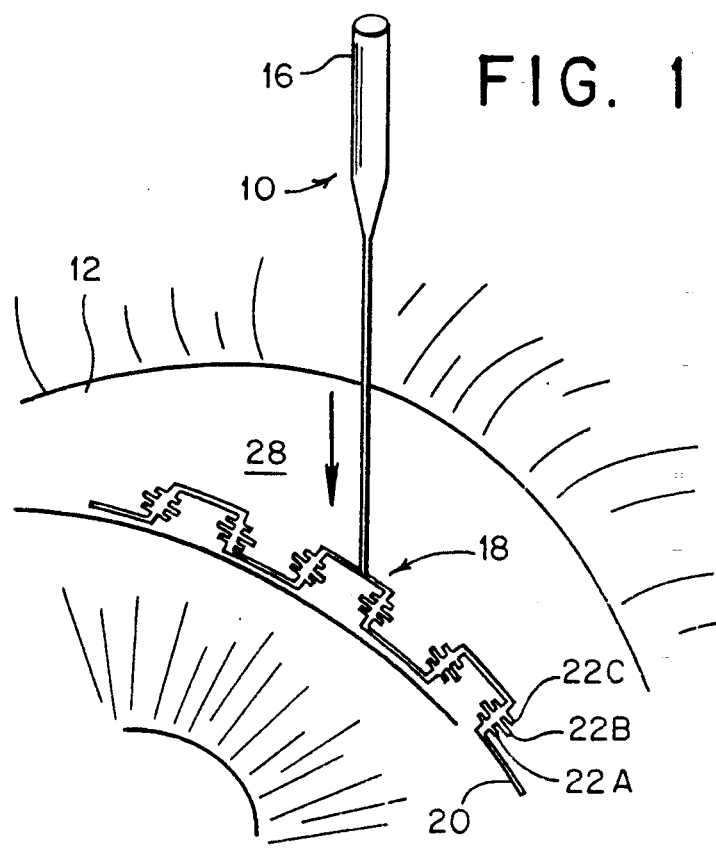
FIG. 1 is an enlarged, fragmentary perspective view of a marking instrument being used to mark the surface of an eye with a dye.
Figure 2:
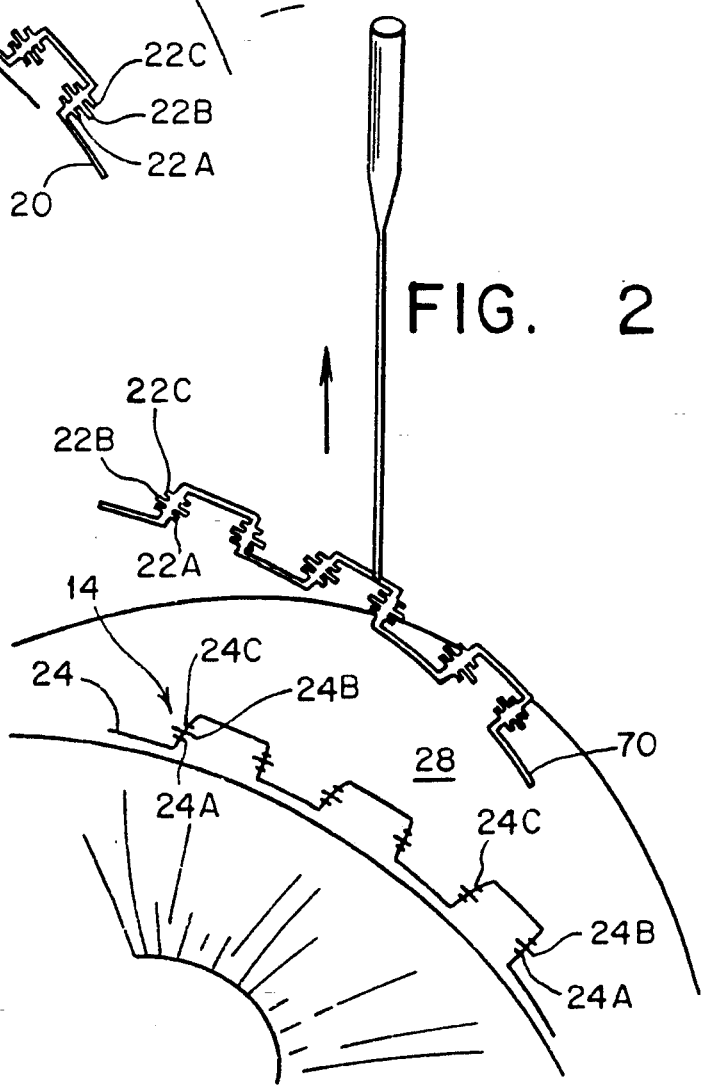
FIG. 2 is a similar view showing the removal of the marking instrument once an incision pattern has been provided upon the eye.

The procedure according to the invention allows an incision to be made in such a manner that it can be tightly closed without affecting the curvature of the cornea unless the surgeon desires to change the curvature thereof. As shown in FIGS. 1-2, a marking tool 10 is provided for marking the eye 12 with a preselected pattern 14. The tool 10 includes a handle 16 and a foot 18. The foot is defined by an elongate wire 20 which has the configuration of a square wave. As discussed below, the wire may alternatively be in the form of a sine wave, triangular wave, or other configuration. The wire may be made from metal or plastic. The bottom surface of the wire should be capable of retaining a dye thereon and transferring the dye to the surface of the sclera as described below. The foot 18 should be slightly arcuate in order to conform to the shape of the eye. Its length should be at least as long as the incision which the surgeon intends to make, e.g. ten to fifteen millimeters.

Each segment of the square wave defined by the wire 20 is about two millimeters in length. This corresponds to the distance between the stitches which are employed to close an ordinary incision made within the eye. The vertical legs of the "square wave" each include three horizontally extending bars 22A, 22B, 22C. The middle bar 22B of each set is considerably longer than the bars 22A, 22C extending above and below it to aid in original alignment.

The marking tool 10 is employed for marking the sclera once the conjunctiva has been cut. It may be packaged as part of a sterile kit including a pad containing a dye such as brilliant green or gentian violet. The dye should be sterile and not readily soluble in water. Once the dye has been applied to the foot 18 of the marking tool, it is transferred to the surface of the eye 12 just beyond the area of the iris by contacting the foot 18 with the sclera as shown in FIG. 1. When the marking tool is withdrawn, as shown in FIG. 2, the pattern 14 formed by the dye remains.

The pattern 14 provides both an outline 24 for making an incision and indicator lines 24A, 24B, 24C for properly aligning the tissue about the incision once an operation has been completed. By following the square wave portion of the pattern 14 shown in FIG. 2 with a diamond knife or the like, an incision 25 is formed which creates a series of "flaps" of tissue. For purposes of clarity, individual flaps 26 are shown in FIGS. 3 and 4A-C. Each of the flaps extends generally perpendicularly with respect to the periphery of the cornea.

Figure 3:
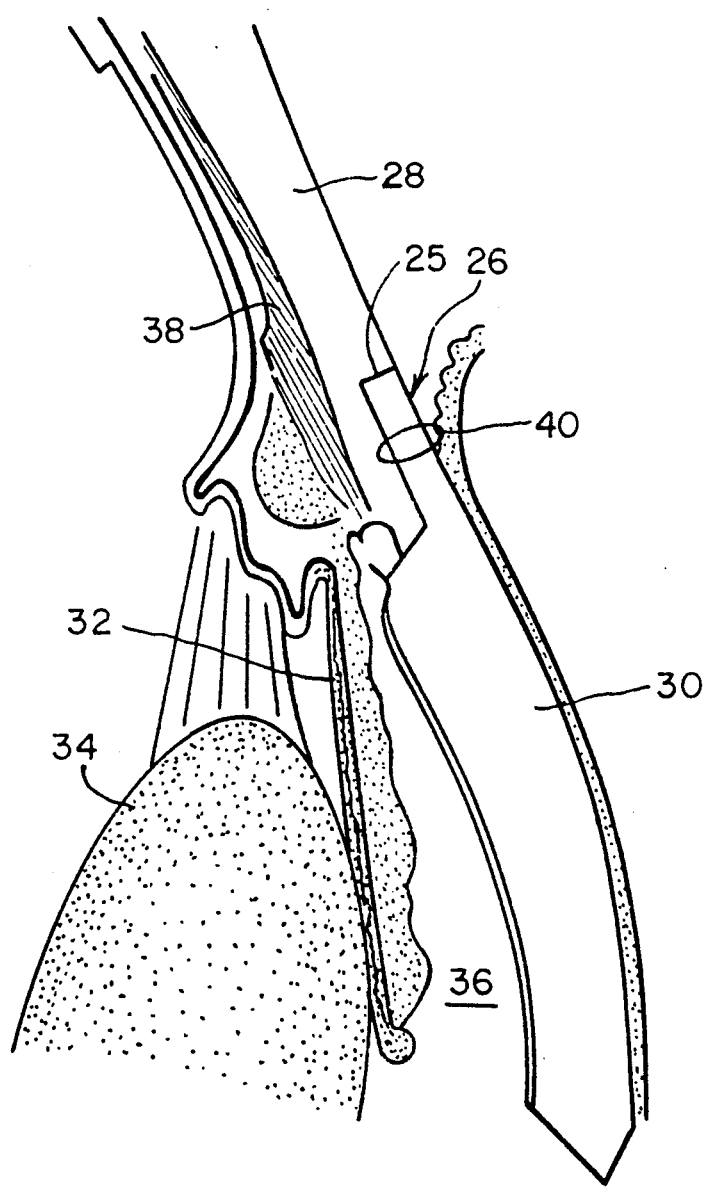
FIG. 3 is an enlarged meridional sectional view of the eye including an incision in the scleral portion thereof.

FIG. 3 is an enlarged, sectional view of a portion of an eye 12 showing the iridocorneal angle. Portions of the eye shown include the sclera 28, cornea 30, iris 32, lens 34, anterior chamber 36, and the ciliary muscle 38. Epithelial layers are also shown. During glaucoma surgery, for example, the surgeon would remove deep tissue beneath one or all of the flaps 26. Cataract surgery typically involves breaking up and removing lens tissue followed by the implantation of an artificial lens.

Figure 4:
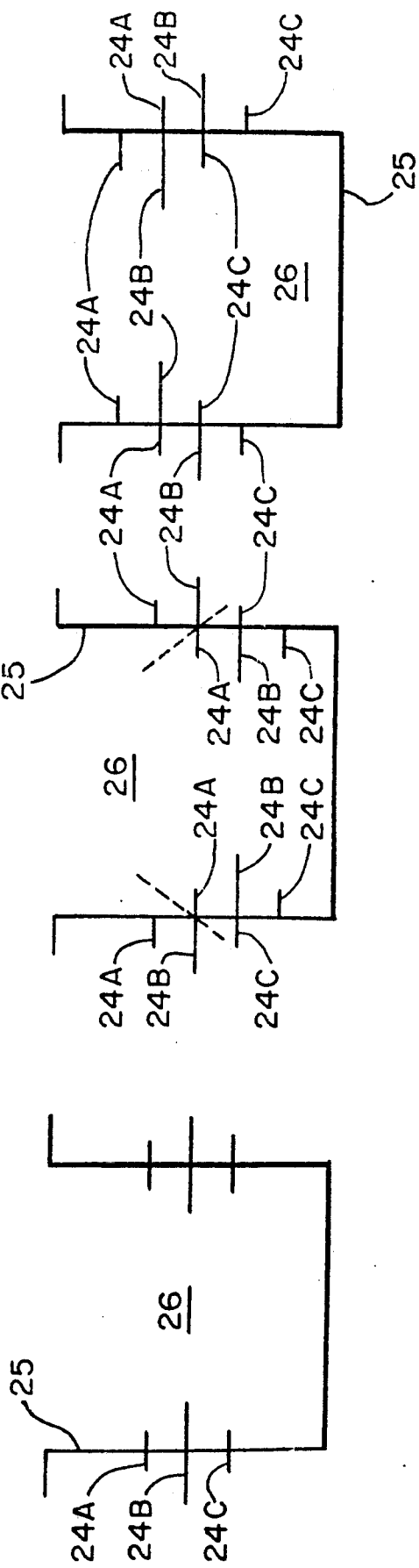
FIGS. 4A–4C show portions of three closed incisions wherein the positions of the indicator lines are in three different relative locations.
Figure 5:
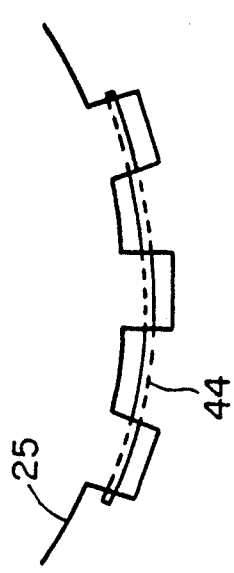
FIGS. 5–9 illustrate five different incision patterns which may be employed in accordance with the invention.

Once the operation has been completed, the incision is sutured. The suturing procedure may be accomplished in several different ways depending upon whether the surgeon desires to change the curvature of the cornea from that which existed prior to the operation. If no change is desired, the stitches 40 are sewn generally parallel to the indicator lines 24A, 24B, 24C of the pattern 14. The relatively long indicator lines 24B should be aligned as closely as possible during the suturing procedure in order to minimize or avoid displacement of the tissue with respect to the incision 25. FIG. 4A illustrates the alignment of the respective indicator lines which is maintained by stitching across each side of the flap in this relatively horizontal direction. FIG. 5 illustrates the orientation of each stitch 40 with respect to the incision. The indicator lines 24A, 24B, 24C are omitted from FIG. 5 for purposes of clarity. If desired, a lock stitch 42 may be provided for closing each flap 26.

If the surgeon desires to apply a force to the cornea, thereby changing the curvature by a selected number of diopters, a pair of diagonal stitches 40', as shown in dotted lines in FIG. 4B, may be employed. When the stitches 40' are tightened, the flap 26 tends to be pulled away from the cornea. The distance between the indicator lines 24A, 24B, 24C should correspond to a certain number of diopters, for example one diopter. As shown in FIG. 4B, the top indicator lines 24A of the flap 26 are aligned with the middle indicator lines 24B extending across the adjoining tissue. The surgeon is accordingly able to determine how much change has been imparted to the curvature of the cornea by which indicator lines upon the flaps 26 are aligned with those of the surrounding tissue.

If the surgeon wishes to urge the flap tissue towards the cornea, as shown in FIG. 4C, diagonal stitches (not shown) are again used, although the surgeon urges the flap towards the cornea upon tying each stitch. The middle indicator lines 24B on each flap 26 can thereby be aligned with the top indicator lines 24A of the surrounding tissue.

When an incision 25 in the form of a square wave is made, as shown in FIG. 5, the stitches 40 used to close the incision will preferably be about two millimeters apart. This is generally the same distance between stitches used to close a conventional incision during eye surgery. If a wound of only a few millimeters needs to be made for a particular operation, the incision may include only one flap 26.

Figure 6:
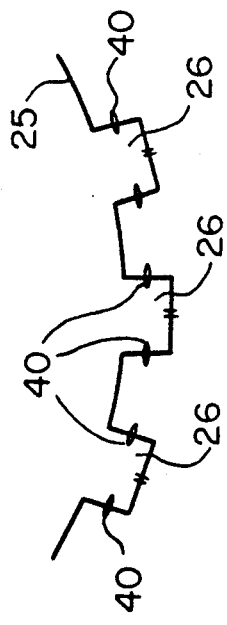

Referring now to FIG. 6, one continuous suture 44 may be employed with multiple passes, instead of individual sutures to close the incision 25. Such a suture can be locked with a single knot. Since the continuous suture follows the contour of the cornea and incision, the curvature of the cornea should be unaffected following such a suturing procedure.

Figure 7:
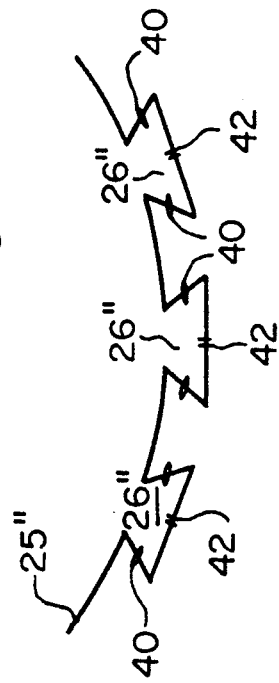
Figure 8:
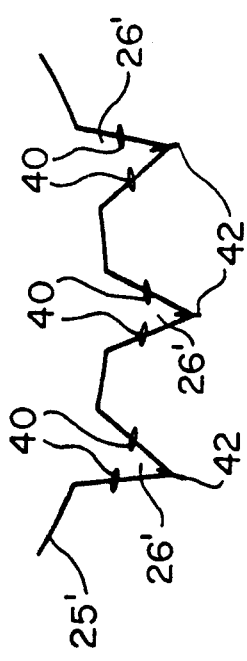
Figure 9:
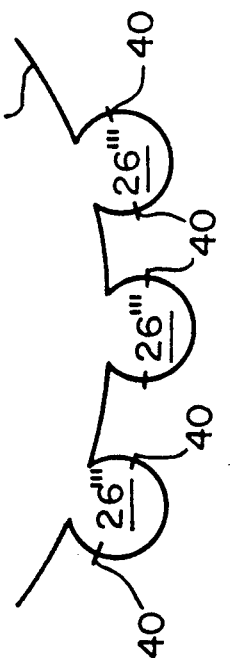

FIGS. 7-9 illustrate various incision patterns which may be employed instead of the square wave pattern discussed above. Indicator lines are omitted from these figures although such lines would be employed therein in the same manner as discussed with respect to FIGS. 4A-4C. FIG. 7 shows an incision 25' resembling a triangular wave. The triangular flaps 26' defined by the pattern each include two opposing incision portions which converge at a point. A lock stitch 42 may be inserted at each point if desired. The stitches 40 closing the opposing incision portions may be parallel to the periphery of the cornea if the curvature thereof is to remain unchanged. In view of the angular orientation of the opposing incision portions defining each flap 26', the stitches may be closed in a direction which is substantially perpendicular to the periphery of the cornea, thereby applying a force thereto and inducing astigmatism.

FIG. 8 shows an incision 25" in the form of a trapezoidal wave. The flaps 26" each have a trapezoidal configuration including opposing incision portions which are closed by stitches 40 once an operation has been completed. Lock stitches 42 may be provided at the base of each flap for closing the flaps without causing a force to be applied to the cornea.

FIG. 9 shows an incision 25''' in the form of a plurality of interconnected, circular flaps 26'''. Opposing incision portions thereof are closed by stitches 40. The stitches for this and all of the above incisions extend down to uninterrupted scleral tissue.

The wave-like incisions discussed above provide greater stability than conventional incisions as their geometries prevent the tissue on opposite sides of the incisions from sliding with respect to each other. The incisions shown in FIGS. 8 and 9 provide two-dimensional stability. If desired, two or more flap configurations may be provided as part of the same incision.

The markings 24A-C, while preferably applied at the same time as the pattern 14, may be applied subsequent thereto. The markings may be discrete, as shown, or extend entirely across the pattern.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of controlling astigmatism during eye surgery comprising:
    forming an incision within eye tissue and within or adjacent to the cornea as a substantially continuous wave extending partially about the cornea, the incision defining a plurality of flaps of tissue between respective, opposing incision portions;
    performing an operation within the eye tissue; and
    suturing the flaps to the surrounding eye tissue following the operation.

2. A method as described in claim 1 including the step of marking the eye tissue with a pattern, and forming the incision by following the pattern with a cutting instrument.

3. A method as described in claim 2 wherein the pattern is formed with a sterile dye.

4. A method as described in claim 1 including the step of suturing the incision such that the flaps are secured in substantially the same positions relative to the surrounding tissue as they were prior to the operation.

5. A method as described in claim 1 including the step of suturing the incision such that the flaps are secured in selected positions which are displaced selected distances with respect to the surrounding tissue from the respective positions of the flaps prior to the operation.

6. A method as described in claim 1 including the step of providing a plurality of markings extending across the incision from the respective flaps to the surrounding tissue, and aligning the markings on opposite sides of the incision upon suturing the flaps, thereby providing a selected force upon the cornea.

7. A method as described in claim 6 including the step of aligning the markings such that substantially no force is applied to the cornea.

8. A method as described in claims 1, 4, 5, 6, or 7 wherein each of the flaps extends generally perpendicularly with respect to the periphery of the cornea.

9. A method as described in claim 1 including the step of providing a marking tool comprising a foot and a handle connected to the foot, the foot including a bottom surface conforming to the outline of the incision to be formed; providing a dye upon the bottom surface of the foot; contacting a selected area of the eye with the bottom surface of the foot, thereby marking the selected area with a pattern, and forming the incision by following the pattern with a cutting instrument.

10. A method of controlling astigmatism during eye surgery, comprising:
    forming an incision within eye tissue such that the incision includes a pair of opposing incision portions extending generally perpendicularly with respect to the periphery of the cornea and a flap of tissue between the opposing incision portions;
    providing a plurality of markings upon the eye tissue, said markings including a plurality of indicator markings on opposite sides of at least one of said pair of incision portions, said indicator markings on opposite sides of said at least one of said incision portions being respectively aligned with each other in a first position when said markings are provided; and
    suturing across said at least one of said pair of incision portions such that said plurality of indicator markings on one side of said incision portion is aligned in a selected manner with said plurality of indicator markings on the opposite side of said incision portion, said indicator markings being moved to a second position upon suturing such that said indicator markings on one side of said at least one of said incision portions are aligned with different indicator markings on the other side of said at least one of said incision portions than were aligned therewith when said markings were provided.

11. A method as described in claim 10 wherein said incision is formed adjacent to the cornea.

* * * * *